(12) United States Patent
Zhu et al.

(10) Patent No.: US 11,185,416 B2
(45) Date of Patent: Nov. 30, 2021

(54) ARTIFICIAL KNEE JOINT

(71) Applicant: Hongwen Zhu, Tianjin (CN)

(72) Inventors: Hongwen Zhu, Tianjin (CN); Guofu Huang, Tianjin (CN); Ronghua Dong, Tianjin (CN); Tianmou Zhu, Tianjin (CN)

(73) Assignee: Hongwen Zhu, Tianjin (CN)

( * ) Notice: Subject to any disclaimer, the term of this patent is extended or adjusted under 35 U.S.C. 154(b) by 29 days.

(21) Appl. No.: 16/628,035

(22) PCT Filed: Jun. 29, 2018

(86) PCT No.: PCT/CN2018/093793
§ 371 (c)(1),
(2) Date: Jan. 2, 2020

(87) PCT Pub. No.: WO2019/007290
PCT Pub. Date: Jan. 10, 2019

(65) Prior Publication Data
US 2020/0383795 A1    Dec. 10, 2020

(30) Foreign Application Priority Data

Jul. 3, 2017    (CN) .......................... 201710530831.3

(51) Int. Cl.
*A61F 2/38* (2006.01)
*A61F 2/30* (2006.01)
*A61F 2/46* (2006.01)

(52) U.S. Cl.
CPC ............ *A61F 2/3836* (2013.01); *A61F 2/389* (2013.01); *A61F 2/3859* (2013.01);
(Continued)

(58) Field of Classification Search
CPC .... A61F 2/3836; A61F 2/3859; A61F 2/3872; A61F 2/389
See application file for complete search history.

(56) References Cited

U.S. PATENT DOCUMENTS

2017/0100254 A1*  4/2017  Lloyd ................... A61F 2/389
2017/0189192 A1*  7/2017  Lloyd ................... A61F 2/3859

FOREIGN PATENT DOCUMENTS

| DE | 3840475 A1 * | 6/1990 | ............... A61F 2/36 |
| EP | 1749505 A1 * | 2/2007 | ........... A61F 2/3868 |
| EP | 2324799 A2 * | 5/2011 | ............... A61F 2/38 |

* cited by examiner

*Primary Examiner* — Brian A Dukert
(74) *Attorney, Agent, or Firm* — CBM Patent Consulting, LLC

(57) ABSTRACT

An artificial knee joint comprises a femoral condyle prosthesis and a tibial plateau prosthesis; wherein the tibial plateau prosthesis includes a medial tibial plateau prosthesis and a lateral tibial plateau prosthesis disposed at both sides of the tibial plateau intercondylar eminence, respectively. The artificial knee joint further comprises a locating pin for fixing the tibial plateau prosthesis. The bottom surface of the tibial plateau prosthesis is provided with a prosthetic notch, and the tibia below the tibial plateau prosthesis is provided with a tibial notch. The prosthetic notch corresponds to the tibial notch, together forming a limiting hole for accommodating the locating pin. The cooperation between the locating pin and the limiting hole can ensure relative position stability and balance between the medial tibial plateau prosthesis and the lateral tibial plateau prosthesis.

5 Claims, 10 Drawing Sheets

(52) U.S. Cl.
CPC .. *A61F 2/3872* (2013.01); *A61F 2002/30133* (2013.01); *A61F 2002/30354* (2013.01); *A61F 2002/30428* (2013.01); *A61F 2002/30546* (2013.01); *A61F 2002/30565* (2013.01); *A61F 2002/4631* (2013.01)

ARTIFICIAL KNEE JOINT

TECHNICAL FIELD

The invention relates to a medical artificial joint prosthesis, particularly relates to an artificial knee joint.

BACKGROUND ART

At present, knee replacement surgery is the world's most fundamental treatment for knee diseases and injuries. In replacement surgery, joint prostheses, also called artificial knee joints, are implanted into the human body to replace the body's natural knee joints. With the gradual advancement of science and technology, further requirements for artificial knee joints and replacement surgery are becoming higher and higher. People hope not only to reduce pain, but also to increase their service life. They also hope to achieve better postoperative recovery, and even hope to reach the level of normal healthy people. For these reasons, various artificial knee joints have gradually come out, and various ideas have been proposed. However, the current mainstream surgical methods and artificial knee joints are far from meeting the above requirements.

The two main leg bones of the human body are the femur and the tibia, with the femur above, the tibia below, and the position where the femur and tibia intersect and interact is the knee joint. The section of the femur in the knee joint is called the lower end of the femur, and the section of the tibia in the knee joint is called the upper end of the tibia; the lower end of the femur and the upper end of the tibia are enlarged, providing a support foundation for the stability of the knee joint.

The lower end of the femur is developed into two discrete condyles, the lower surfaces of the condyles are smoothly rounded and covered in articular cartilage. The two discrete condyles are not symmetrical, the medial condyle is larger, and the lateral condyle is smaller, so as to adapt to different stress situations of the medial and lateral sides. The upper end of the tibia comprises shallow concave lateral and medial plateau which covered with articular cartilage. The medial plateau is larger than the lateral plateau. The entire tibial plateau is separated by an eminence or tubercle between the lateral plateau and the medial plateau.

The patella (kneecap) is embedded in the quadriceps tendon which connects the quadriceps musculature of the anterior upper thigh to the patella, and the patella being connected by the patellar ligament to the tibia just beneath the knee joint. The combination of the quadriceps tendon, patella, and patellar ligament acts rather like a pulley, transmitting forces generated by the quadriceps musculature to the tibia via the flexed knee, thereby straightening the leg or decelerating the rate of flexion. The patella obviously also serves the further function of protecting the knee joint from impact damage.

The cruciate ligaments act to substantially locate the condyles on the tibia during flexion and extension. During flexion of the knee joint, tension applied by the anterior cruciate ligament restrains the condyles from posterior displacement. During extension of the knee joint, the posterior cruciate ligament restrains the condyles from anterior displacement.

The knee menisci are vital to the normal functioning of the knee joint. In addition to enhancing joint congruence, the menisci cushion and differentiate forces as they pass through the knee joint, reducing the friction and impact between the femur and tibia.

However, in the current popular knee replacement surgery, the natural tibial plateau is often directly removed, replaced with an artificial tibial plateau, and a similarly shaped femoral condyle prosthesis is installed on the femoral surface, so that the new femoral condyle prosthesis interact with the artificial tibial plateau, which lead to the absence of cruciate ligaments and menisci in the knee joint after surgery, and some even the patella. Therefore, the current surgical method and the characteristics of the corresponding artificial knee joint make it impossible to have the desired recovery effect after such an operation. Such surgery destroys the original physiological structure and characteristics of the knee joint, and causes permanent irreversible damage to the knee joint.

Adjustments are urgently needed and a new artificial knee joint capable of retaining the cruciate ligaments, the patella and having a meniscus cushioning function is needed.

In addition, after years of clinical research, it is known that in knee joint lesions, the medial condyle and lateral condyle, the medial plateau and the lateral plateau have different degrees of injury, which are often affected by human behavior and work habits. The medial condyle or plateau is damaged first, and then the other condyle or plateau is accelerated and the patient suffers great pain during this process. If surgery is performed during this process, the side that is not damaged is often removed together because the tibial plateau and the new femoral condyle are monolithic; moreover, most knee joint lesions are caused by meniscus, femoral condyle or tibial plateau degeneration and wear, with minimal damage to the cruciate ligaments and the patella.

For this reason, some people have proposed to replace the existing monolithic knee joint with a semi-condylar knee joint. Although this idea is worth promoting, it encountered great difficulties in the actual implementation process, which ultimately could not be achieved, or its real effect was lower than the original monolithic knee joint; the main problem is that when the semi-condylar knee joint is replaced, the replacement part does not match the function and height of the intact part, which cannot effectively delay the damage rate of the intact part. After the other intact part of the knee joint is also damaged, the artificial knee joint still needs to be replaced by surgery. At this time, if the semi-condylar knee joint is also used, the two semi-condylar knee joints are difficult to coordinate in terms of height, size and elasticity, and the use effect is poor. If the monolithic knee joint is used to replace, the originally replaced semi-condylar knee joint becomes meaningless, and it also involves the secondary damage installation of the tibia and femur.

Due to the above problems, the present inventors have made in-depth research on the existing artificial knee joints and devised a new artificial knee joint to solve the above problems.

Contents of the Invention

In order to overcome the above problems, the present inventors have conducted intensive research and devised an artificial knee joint. The knee joint includes a femoral condyle prosthesis and a tibial plateau prosthesis, and said tibial plateau prosthesis includes a medial tibial plateau prosthesis and a lateral tibial plateau prosthesis respectively disposed at both sides of the tibial plateau intercondylar eminence. The artificial knee joint further includes a locating pin for fixing the tibial plateau prosthesis. The bottom surface of said tibial plateau prosthesis is provided with a prosthetic notch, and a tibia below said tibial plateau prosthesis is provided with a tibial notch. Said prosthetic notch corresponds to said tibial notch, together forming a limiting hole for accommodating the locating pin. Said limiting hole penetrates the tibial plateau intercondylar eminence and connects the medial tibial plateau prosthesis and the lateral tibial plateau prosthesis. The artificial knee joint further includes a locating pin that can be embedded in the limiting hole, and the cooperation between the locating pin and the limiting hole can ensure relative position stability and balance between the medial tibial plateau prosthesis and the lateral tibial plateau prosthesis, thereby completing the present invention.

Specifically, the object of the present invention is to provide an artificial knee joint, the knee joint includes a femoral condyle prosthesis 1 and a tibial plateau prosthesis 2.

Said tibial plateau prosthesis 2 includes a medial tibial plateau prosthesis 201 and a lateral tibial plateau prosthesis 202 independently of each other.

Said medial tibial plateau prosthesis 201 and said lateral tibial plateau prosthesis 202 are respectively disposed at both sides of the tibial plateau intercondylar eminence 1 and are located below the femoral condyle prosthesis 1.

Wherein, said tibial plateau prosthesis 2 is placed at the lower back of the patella.

Wherein, the artificial knee joint further includes a locating pin 5, through said locating pin 5 the medial tibial plateau prosthesis 201 and the lateral tibial plateau prosthesis 202 are fixed to the upper end of the tibia.

Wherein, said locating pin 5 passes through the tibial plateau intercondylar eminence 31, an upper portion of one end thereof is installed in the medial tibial plateau prosthesis 201, and an upper portion of the other end thereof is installed in the lateral tibial plateau prosthesis 202.

Wherein, a prosthetic notch 23 is provided on the bottom of said medial tibial plateau prosthesis 201 and said lateral tibial plateau prosthesis 202.

A tibial notch 32 is provided on the top of the tibia below the tibial plateau prosthesis 2, and Said prosthetic notch 23 and said tibial notch 32 together constitute a limiting hole 4 for accommodating the locating pin 5, and the limiting hole penetrates the tibial plateau intercondylar eminence 31.

Wherein, both said medial tibial plateau prosthesis 201 and said lateral tibial plateau prosthesis 202 include an upper gasket 21 and a lower gasket 22 respectively.

Wherein, an elastic subassembly 6 is provided on the lower gasket 22, and through which the impact force transmitted from the femoral condyle prosthesis 1 to the upper gasket of the tibial plateau prosthesis 2 is cushioned, so that the upper gasket 21 has a meniscus-like function.

Wherein, said elastic subassembly 6 penetrates the lower gasket 22, and is fixed and installed on the lower gasket 22, the upper end protrudes above the lower gasket 22 and abuts on the lower surface of the upper gasket.

Wherein, said elastic subassembly 6 includes a sleeve 61 and a spring 62, the lower end of the spring 62 is buried in the sleeve 61, and the upper end of the spring is abutted on the lower surface of the upper gasket.

The sleeve 61 passes through the lower gasket 22, and the bottom end of the sleeve is installed in the cavity 7 of the tibia.

Wherein, a bolt 63 for adjusting the elasticity of the spring 62 is provided at the bottom of the sleeve 61.

The present invention provides a method for using an artificial knee joint described above, and the method includes the following steps:

Step 1, install the femoral condyle prosthesis 1 on the femoral condyle;

Step 2, open a space for the placement of the tibial plateau prosthesis 2 on the tibial plateau;

Step 3, excavate a tibial notch 32 in the tibia and extend the tibial notch 32 to the tibial plateau intercondylar eminence 31, and form an intercondylar eminence hole 33 in the tibial plateau intercondylar eminence 31;

Step 4, excavate a cavity 7 in the tibia;

Step 5, insert the sleeve on the tibial plateau prosthesis 2 into the cavity 7, and simultaneously adjust the relative positions of the prosthetic notch 23, the tibial notch 32 and the intercondylar eminence hole 33, so that the prosthetic notch 23, the tibial notch 32 and the intercondylar eminence hole 33 together constitute a limiting hole 4;

Step 6, install the locating pin 5 in the limiting hole 4, after the locating pin 5 is fixed, the tibial plateau prosthesis 2 is fixed by bone cement.

Wherein, preferably, before performing Step 5, adjust the elasticity of the spring 62 by rotating the bolt 63.

The beneficial effects of the present invention include:

(1) The artificial knee joint provided according to the present invention has two discrete medial tibial plateau prosthesis and lateral tibial plateau prosthesis, which can be placed at both sides of tibial plateau intercondylar eminence, thereby eliminating the need to remove and destroy the tibial plateau intercondylar eminence, ensuring the cruciate ligaments on the tibial plateau intercondylar eminence can be kept intact, so that greatly enhances the use effect and the patient experience;

(2) The artificial knee joint provided according to the present invention has two discrete medial tibial plateau prosthesis and lateral tibial plateau prosthesis, which can be implanted in stages according to the patient's condition, and the practical application is more flexible and convenient;

(3) The tibial plateau prosthesis of the artificial knee joint provided according to the present invention is provided with an elastic subassembly, which can simulate the function of the meniscus and provide a cushioning effect, so that the artificial knee joint is more substantially similar to the natural knee joint;

(4) The elasticity/elastic force of the spring in the elastic subassembly of the tibial plateau prosthesis of the artificial knee joint provided according to the present invention can be adjusted according to different ages and physical conditions, which can ensure that the spring elasticity/elastic force is in an optimal state;

(5) The elastic subassembly of the tibial plateau prosthesis in the artificial knee joint provided according to the present invention is arranged in a downwardly protruding tubular structure, which is embedded in the cavity on the tibia, so as to also play a role in limiting and fixing the tibial plateau prosthesis;

(6) The tibial plateau prosthesis of the artificial knee joint provided according to the present invention is provided with a prosthetic notch, and also provided with a locating pin connecting the medial tibial plateau prosthesis and the lateral tibial plateau prosthesis and passing through the tibial plateau intercondylar eminence, so that the relative position between the two tibial plateau prostheses are limited and fixed in an all-round way, making the artificial knee joint balanced in force, stable overall, long service life and good patient experience;

(7) The artificial knee joint provided according to the present invention only replaces a small part of the femur and tibia. It does not damage or destroy other physiological components near the femur and tibia, does not affect its normal physiological function, and can retain related physiological structures in the knee joint such as the patella, the cruciate ligaments, and the like, thereby having a good postoperative recovery effect.

DESCRIPTION OF THE REFERENCE SIGNS

1—femoral condyle prosthesis;
101—medial femoral semi-condylar prosthesis;
102—lateral femoral semi-condylar prosthesis;
11—anterior button cover;
12—fixing spine;
13—posterior button cover;
14—fixing pin;
2—tibial plateau prosthesis;
201—medial tibial plateau prosthesis;
202—lateral tibial plateau prosthesis;
21—upper gasket;
22—lower gasket;
23—prosthetic notch;
3—tibia;
31—tibial plateau intercondylar eminence;
32—tibial notch;
33—intercondylar eminence hole;
4—limiting hole;
5—locating pin;
6—elastic subassembly;
61—sleeve;
62—spring;
63—bolt;
7—cavity;
8—femur.

Specific Embodiments for Carrying out the Invention

Hereinafter, the present invention will be explained in more detail with reference to figures and examples. Through these explanations, the features and advantages of the present invention will become clearer.

The term "exemplary" as used herein is intended to be "serving as an example, an embodiment, or an illustrative embodiment". Any of the embodiments described herein as "exemplary" need not be construed as preferred as or better than other embodiments. Although various aspects of the embodiments are shown in the figures, it is not necessary to draw a figure in proportion unless otherwise specified.

Figure 1:
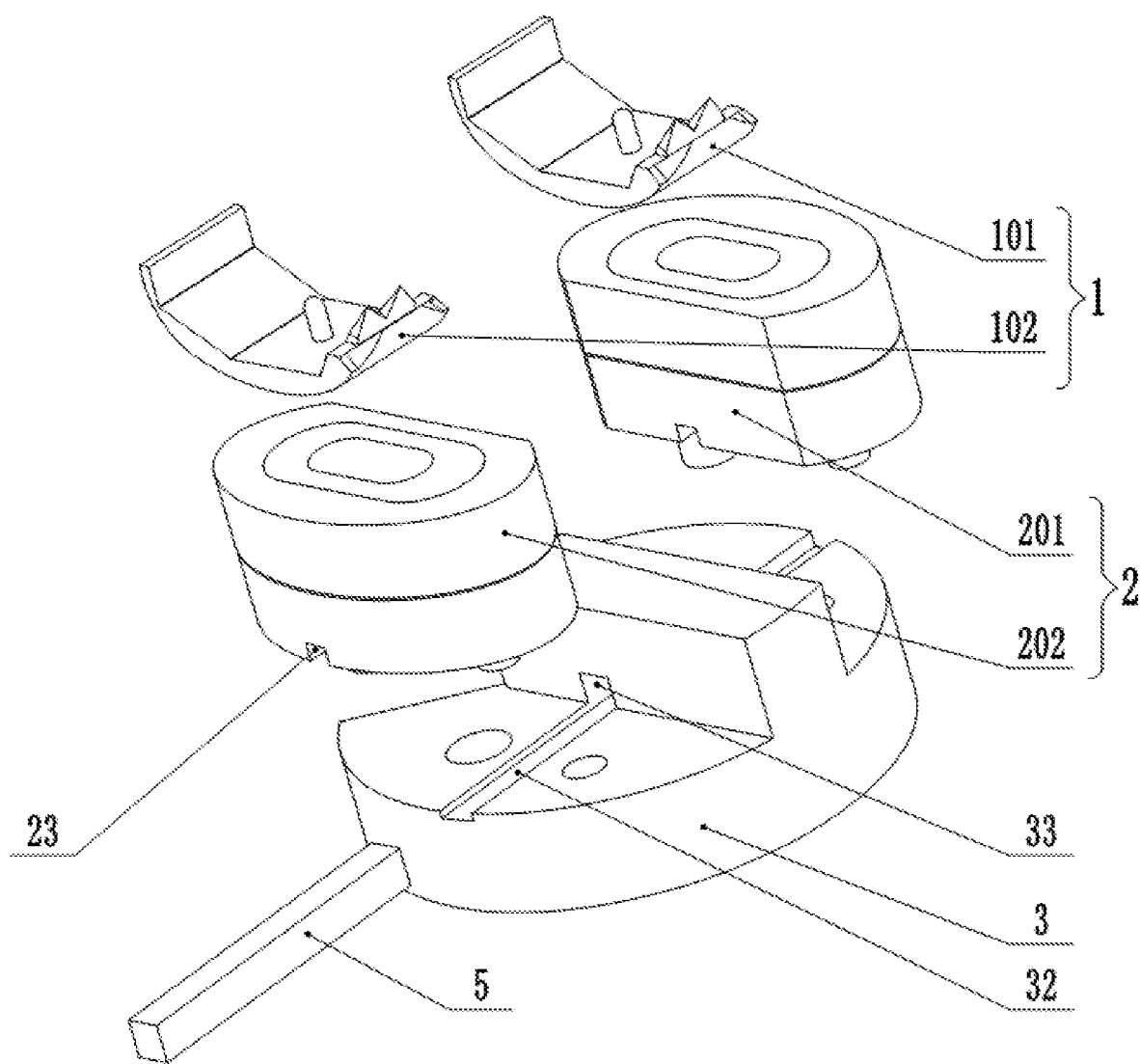
FIG. 1 shows an exploded view of an artificial knee joint assembly according to a preferred embodiment of the present invention.

The artificial knee joint provided according to the present invention is shown in FIG. 1. The artificial knee joint includes a femoral condyle prosthesis 1 and a tibial plateau prosthesis 2, wherein, the femoral condyle prosthesis 1 is disposed at the lower end of the femur 8 and replaces a part of the bone structure at the lower end of the femur, and the tibial plateau prosthesis 2 is disposed at the upper end of the tibia 3 and replaces a part of the bone structure on the tibial plateau at the upper end of the tibia; in this application, said tibial plateau is the surface on the tibia that contacts the lower end of the femur, and in the center of the tibial plateau is a tibial plateau intercondylar eminence 31, also referred to as a eminence or tubercle, to which cruciate ligaments are attached. The tibial plateau is mainly composed of a medial plateau and a lateral plateau at both sides of said tibial plateau intercondylar eminence.

Said tibial plateau prosthesis 2 includes a medial tibial plateau prosthesis 201 and a lateral tibial plateau prosthesis 202 independently of each other, which are respectively used to replace the medial plateau and the lateral plateau. After said tibial plateau prosthesis replaces the medial plateau and/or the lateral plateau, the height of the unreplaced part (including the tibial plateau intercondylar eminence) of the tibial plateau has the same height of the tibial plateau prosthesis, that is, after replacing a part of the tibial structure through the tibial plateau prosthesis, the tibial height and shape have no change.

Figure 2:
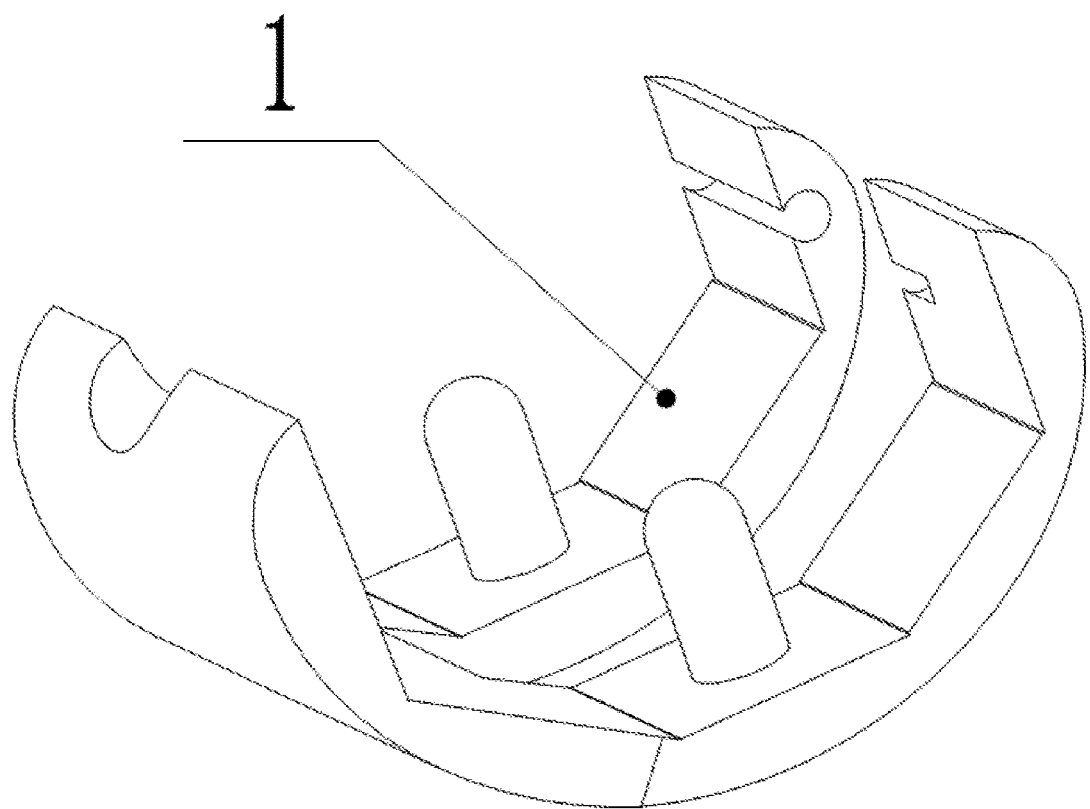
FIG. 2 shows a schematic structural diagram of a commonly used monolithic femoral prosthesis in the prior art artificial knee joint.

Said femoral condyle prosthesis may be prosthesis with two discrete single condyles or a full condyle connected as a whole. FIG. 2 shows a fully-condylar femoral prosthesis connected as a whole, the volume and weight of the femoral prosthesis is large, and will block the femoral trochlear due to the track change of the trochlear, rub against the patella, often require artificial patella replacement to ensure its normal work.

In the present invention, preferably, said femoral condyle prosthesis includes two discrete single condyles, and respectively are a medial femoral semi-condylar prosthesis 101 and a lateral femoral semi-condylar prosthesis 102, that is, the medial femoral semi-condylar prosthesis 101 and the lateral femoral semi-condylar prosthesis 102 are independent of each other; the medial femoral semi-condylar prosthesis 101 is installed on the medial condyle of femur, and abuts on the top surface of the medial tibial plateau prosthesis 201; the lateral femoral semi-condylar prosthesis 102 is installed on the lateral condyle of femur, and abuts on the top surface of the lateral tibial plateau prosthesis 202.

Figure 3:
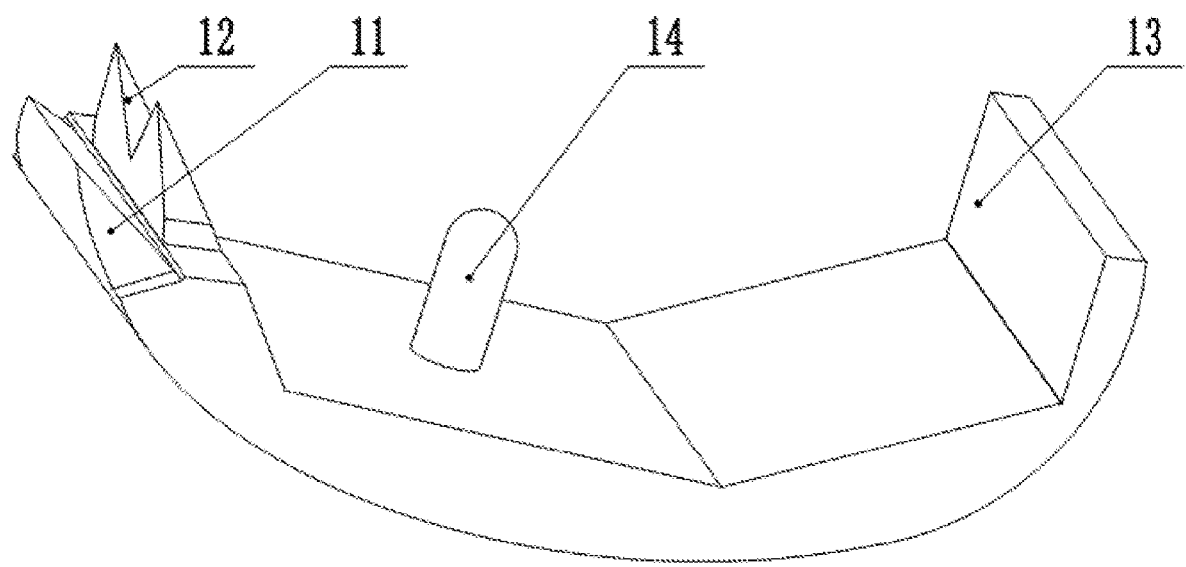
FIG. 3 shows a schematic structural diagram of a medial femoral semi-condylar prosthesis or lateral femoral semi-condylar prosthesis in an artificial knee joint according to a preferred embodiment of the present invention.

The medial femoral semi-condylar prosthesis 101 and the lateral femoral semi-condylar prosthesis 102 of the femoral condyle prosthesis are basically similar in overall shape and composition, and the two are approximately mirror-symmetrical. Due to the size and shape of the medial condyle of femur and lateral condyle of femur are slightly different, so the corresponding medial femoral semi-condylar prosthesis 101 and lateral femoral semi-condylar prosthesis 102 are not completely symmetric. Because the components of the medial femoral semi-condylar prosthesis 101 and the lateral femoral semi-condylar prosthesis 102 are basically the same, the medial femoral semi-condylar prosthesis 101 is now described as an example, which includes an anterior button cover 11, a fixing spine 12, a posterior button cover 13 and a fixing pin 14, as shown in FIG. 1 and FIG. 3.

Figure 11:
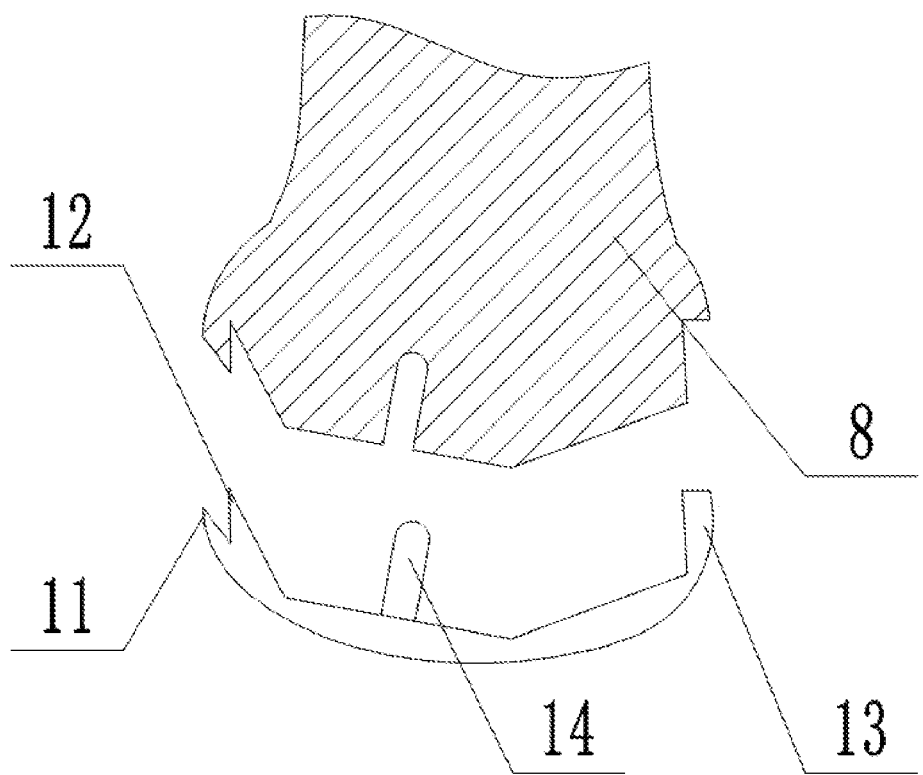
FIG. 11 shows an exploded view of the assembly of a femoral condyle prosthesis and a femur in an artificial knee joint according to a preferred embodiment of the present invention.
Figure 12:
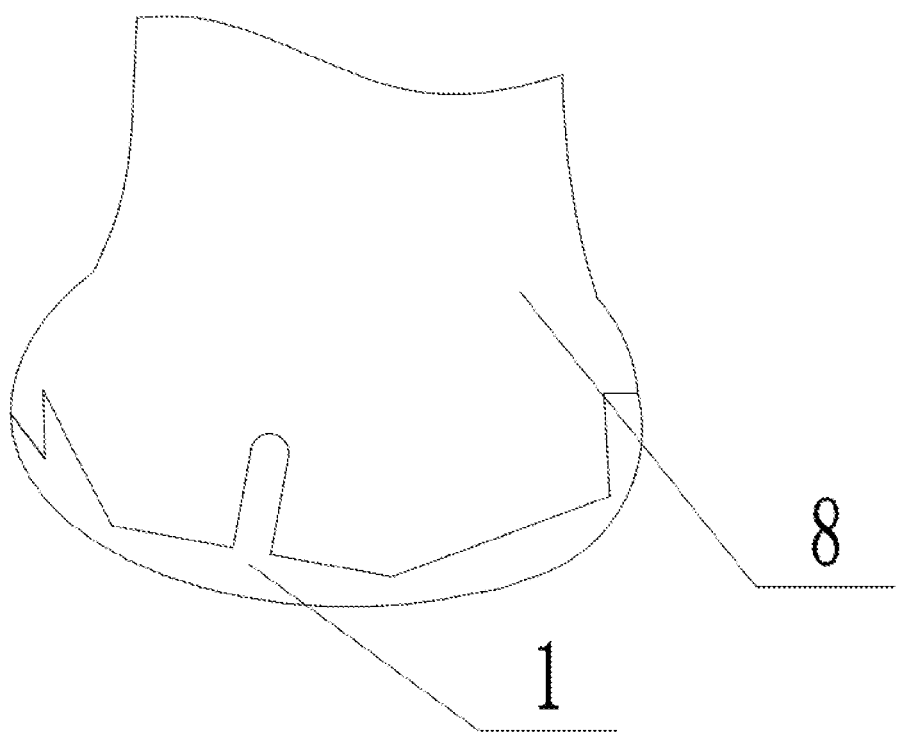
FIG. 12 shows a schematic structural diagram of a femoral condyle prosthesis and a femur assembled in an artificial knee joint according to a preferred embodiment of the present invention.

Specifically, the shape of said medial femoral semi-condylar prosthesis 101 is consistent with the shape of the replaced part of the femur, and the outer surface is in the shape of an arc, as shown in FIG. 11 and FIG. 12. An anterior button cover 11 and a posterior button cover 13 are respectively provided at two ends of the medial femoral semi-condylar prosthesis 101 to fix the medial femoral semi-condylar prosthesis 101 to the femur. Wherein, the top end of the posterior button cover 13 is inclined toward the anterior button cover.

When installing said femoral condyle prosthesis, a concave prosthetic fixation area is first excavated from the femur. After the femoral condyle prosthesis is installed in the area, the area can be filled up just so that the femur can be restored to the previous state before the prosthetic fixation area was excavated. That is, the medial femoral semi-condylar prosthesis 101 is fixed to the femur by being embedded in the prosthetic fixation area.

The medial femoral semi-condylar prosthesis 101 and the lateral femoral semi-condylar prosthesis 102 are respectively provided with a fixing spine 12 and a fixing pin 14 on the inner side. When the prosthetic fixation area is processed on the femur, a blind hole is also excavated in the cancellous bone at the corresponding position. When the medial femoral semi-condylar prosthesis 101 or the lateral femoral semi-condylar prosthesis 102 is fastened to the prosthetic fixation area, the fixing pin 14 is embedded in the blind hole.

At the same time, on the cancellous bone, a tapered groove/conical hole is opened near the anterior cortical bone, wherein, said anterior cortical bone refers to the cortical bone in contact with the anterior button cover 11. The specific shape and number of the tapered groove/conical hole correspond to the shape and number of the fixing spine 12. When the medial femoral semi-condylar prosthesis 101 or the lateral femoral semi-condylar prosthesis 102 is fastened to the prosthetic fixation area, the fixing spine 12 is sharply inserted into the tapered groove/conical hole.

Preferably, the pore size of the blind hole is slightly smaller than the outer diameter of the fixing pin 14 and in the process of embedding the fixing pin 14 into the blind hole, the pore size of the blind hole will be forced to expand and compress the cancellous bone area, thereby forming a tight consolidation.

Preferably, said fixing spine 12 and fixing pin 14 may be one or more. In the present application, preferably, there are two fixing spines 12 and one fixing pin 14. Accordingly, the number of the blind hole and the tapered groove/conical hole matches the number of the fixing pin 14 and the fixing spine 12.

The area on the femur that is in contact with the anterior button cover 11 and the posterior button cover 13 is the cortical bone area, which has high strength and toughness. In the present invention, it is further preferred that the anterior button cover 11 is adjacent to said fixing spine 12, the anterior button cover 11 is buckled on the outside of the cortical bone, the fixing spine 12 is inserted into the cancellous bone, and topped on the cortical bone from the inside, thereby tightening the cortical bone and forming a socket with the posterior button cover 13 and then fasten and fix on the femur. At the same time, the anterior button cover 11 and said fixing spine 12 together form a groove-shaped structure with a V-shaped cross section, and the cortical bone that has been ground on the femur is pressed against the bottom of the groove-shaped structure. The fixing spine 12 and the groove-shaped structure with a V-shaped cross section jointly assist the fixation of the anterior button cover 11 to the cortical bone, so that the anterior button cover 11 and the posterior button cover 13 can be buckled on the femur, which can be scientifically and reasonably make the femoral condyle prosthesis and the femur consolidate firmly and reliably, and can withstand a long test.

In a preferred embodiment, the surface area of the femoral condyle prosthesis is small, so the volume and weight are small. Specifically, the outer surface area of the medial femoral semi-condylar prosthesis 101 accounts for less than 60% of the outer surface area of the medial condyle of femur, preferably about 40% to 55%, and in this application preferably about 50%. Similarly, the outer surface area of the lateral femoral semi-condylar prosthesis 102 accounts for less than 60% of the outer surface area of the lateral condyle of femur, preferably about 40% to 55%, and in this application preferably about 50%.

Said medial femoral semi-condylar prosthesis 101 and the lateral femoral semi-condylar prosthesis 102 are located at both sides of the femoral trochlear, and the replacement of the medial femoral semi-condylar prosthesis 101 and the lateral femoral semi-condylar prosthesis 102 does not affect the normal work of the femoral trochlear. Therefore, replacing the medial femoral semi-condylar prosthesis 101 and the lateral femoral semi-condylar prosthesis 102 has no effect on the normal work and installation position of the patella.

Figure 9:
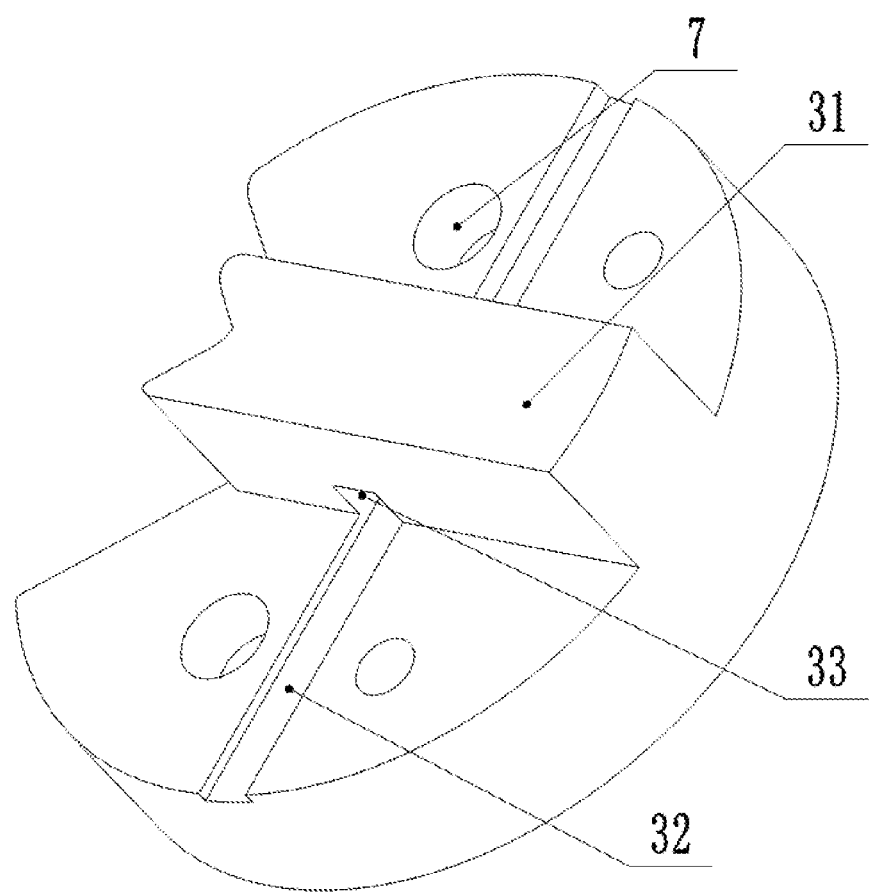
FIG. 9 shows a schematic structural diagram of a tibia on which tibial plateau prostheses are placed in an artificial knee joint according to a preferred embodiment of the present invention.
Figure 10:
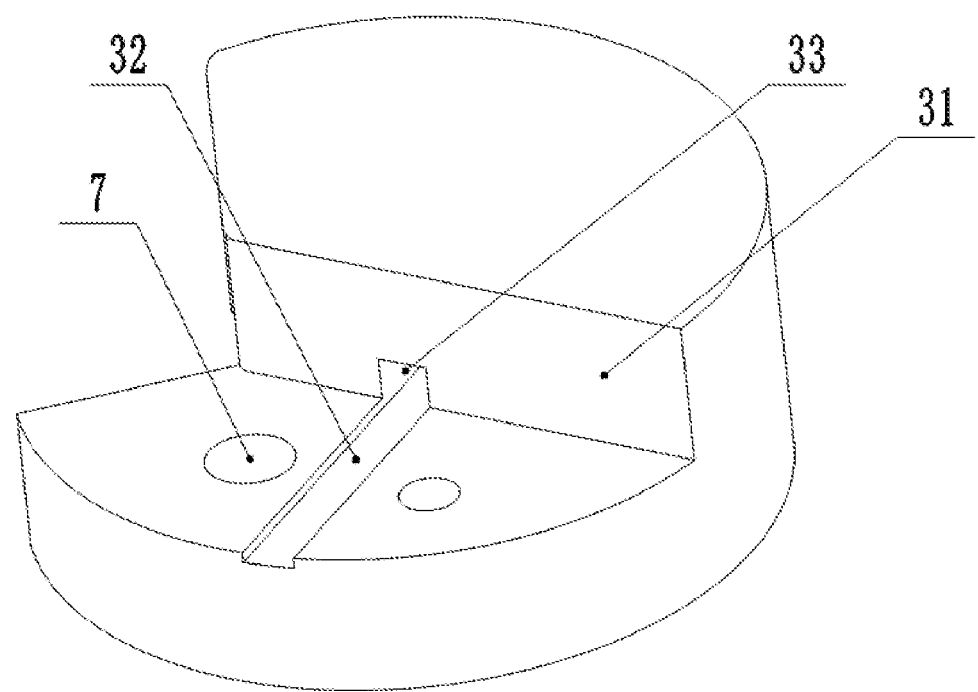
FIG. 10 shows a schematic structural diagram of a tibia on which a medial tibial plateau prosthesis or lateral tibial plateau prosthesis is placed in an artificial knee joint according to a preferred embodiment of the present invention.

In the present invention, preferably, said tibial plateau prosthesis includes a medial tibial plateau prosthesis 201 and a lateral tibial plateau prosthesis 202, said medial tibial plateau prosthesis 201 and lateral tibial plateau prosthesis 202 are respectively disposed at both sides of the tibial plateau intercondylar eminence 31 and located below the femoral condyle prosthesis 1. The tibial plateau prosthesis 2 replaces the medial plateau and lateral plateau in the tibial plateau and supports the femoral condyle prosthesis 1. In order to place and fix said two tibial plateau prostheses, it is necessary to make a certain structural reconstruction to the tibia or the tibial plateau. The reconstructed tibia is also called tibial plateau, as shown in FIG. 9. When only the medial tibial plateau prosthesis 201 or the lateral tibial plateau prosthesis 202 of said tibial plateau prosthesis is replaced, the reconstructed tibia or tibial plateau is shown in FIG. 10.

The upper surface of said tibial plateau prosthesis 2 has inward and downward depressions to facilitate cooperation with the femur, similar to the medial plateau and lateral plateau on a natural tibial plateau, as shown in FIG. 1.

The cross-section of said tibial plateau prosthesis 2 is of a kidney type or a kidney-like type, and its outer contour is consistent with the excavated part of the tibial plateau.

The cross-sectional size of said tibial plateau prosthesis 2 is about one third of the cross-sectional size of the tibial plateau.

In a preferred embodiment, the artificial knee joint further includes a locating pin 5 for fixing the tibial plateau prosthesis 2, by which the medial tibial plateau prosthesis 201 and the lateral tibial plateau prosthesis 202 are fixed to the tibia, as shown in FIG. 1.

Preferably, said locating pin 5 passes through the tibial plateau intercondylar eminence 31, and an upper portion of one end thereof is installed in the medial tibial plateau prosthesis 201 and an upper portion of the other end is installed in the lateral tibial plateau prosthesis 202.

Figure 7:
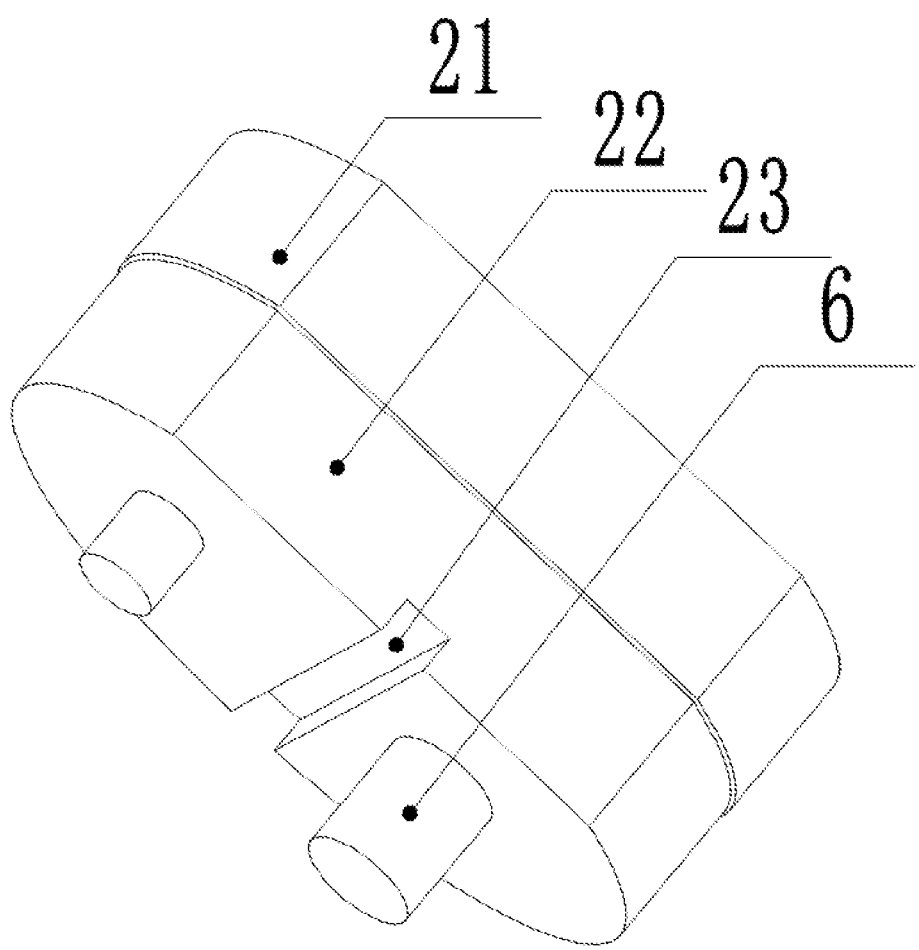
FIG. 7 shows a schematic structural diagram of a medial tibial plateau prosthesis in an artificial knee joint according to a preferred embodiment of the present invention.

In a preferred embodiment, as shown in FIG. 7, a prosthetic notch 23 is provided on the bottom of said tibial plateau prosthesis 2.

A tibial notch 32 is provided on the top of the tibia below the tibial plateau prosthesis 2; that is, a tibial notch 32 is provided on the tibia/tibial plateau below said tibial plateau prosthesis, and the tibial notch 32 passes through or penetrates the tibial plateau intercondylar eminence 31, that is, an intercondylar eminence hole 33 is provided on said tibial plateau intercondylar eminence, and the intercondylar eminence hole 33 is a through hole; as shown in FIG. 9 and FIG. 10.

Figure 4:
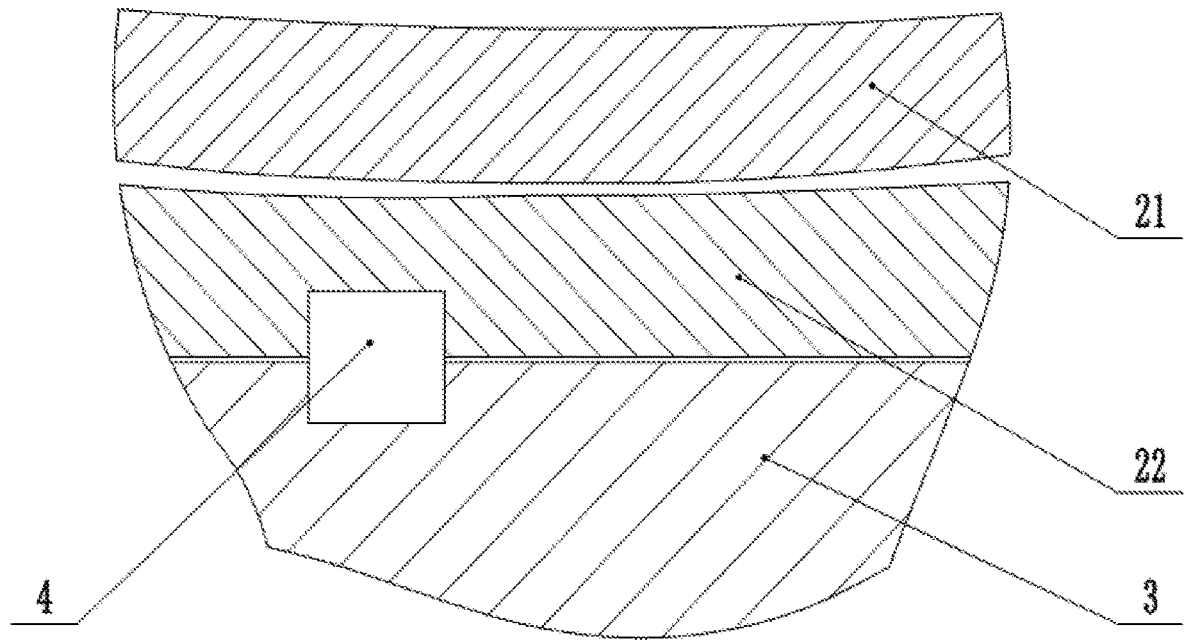
FIG. 4 shows a schematic diagram of a sectional shape of a limiting hole/locating pin in an artificial knee joint according to a preferred embodiment of the present invention.
Figure 5:
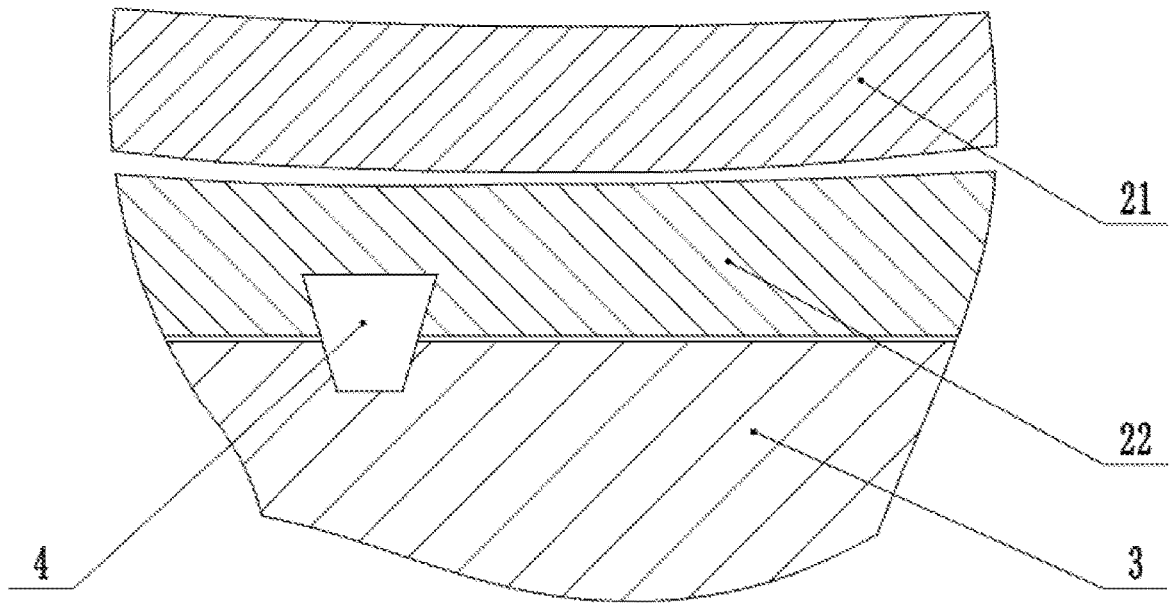
FIG. 5 shows a schematic diagram of a sectional shape of a limiting hole/locating pin in an artificial knee joint according to a preferred embodiment of the present invention.
Figure 6:
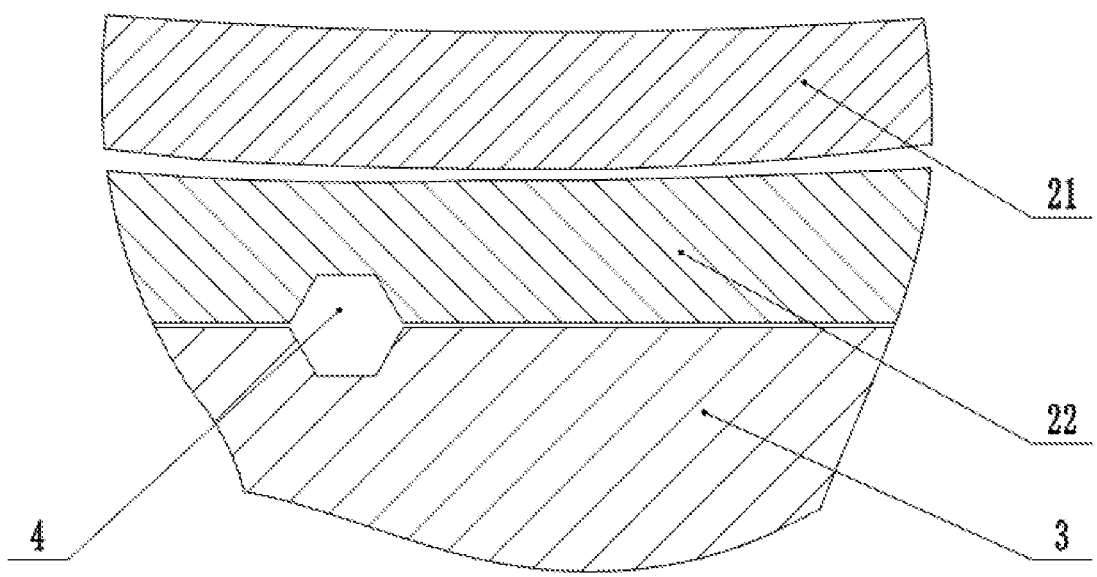
FIG. 6 shows a schematic diagram of a sectional shape of a limiting hole/locating pin in an artificial knee joint according to a preferred embodiment of the present invention.

Said prosthetic notch 23 corresponds to the tibial notch 32, and together with the intercondylar eminence hole 33 constitutes a limiting hole 4 for accommodating said locating pin 5, as shown in FIG. 4, FIG. 5, and FIG. 6.

Preferably, said limiting hole 4 and locating pin 5 penetrate the tibial plateau intercondylar eminence 31 and connect the medial tibial plateau prosthesis 201 and the lateral tibial plateau prosthesis 202; that is, in the axial direction of said limiting hole 4, the limiting hole is made up of three parts, wherein, the two parts at the two ends are enclosed by the prosthetic notch 23 above and the tibial notch 32 below; the third part in the middle is completely an intercondylar eminence hole 33 opened on the tibial plateau intercondylar eminence 31.

In a preferred embodiment, the length value of the locating pin is greater than the length value of the prosthetic notch 23 on the medial tibial plateau prosthesis 201 or the lateral tibial plateau prosthesis 202, and the length value of the locating pin is less than the sum of the length value of one prosthetic notch 23 and the width value of the tibial plateau intercondylar eminence 31. Therefore, when only the medial tibial plateau prosthesis 201 or the lateral tibial plateau prosthesis 202 is installed, the locating pin can satisfy the positioning and fixing effect. When the medial tibial plateau prosthesis 201 and the lateral tibial plateau prosthesis 202 are installed, the length of said limiting hole 4 naturally extends accordingly, the locating pin can be further moved into the extended limiting hole, and completely penetrates the tibial plateau intercondylar eminence 31 ultimately. Both ends of the locating pin are embedded in the prosthetic notch 23 and play a role in limiting and fixing the tibial plateau prosthesis 2. It is worth noting that due to the existence of the locating pin, it can position the medial tibial plateau prosthesis 201 and the lateral tibial plateau prosthesis 202 at both sides of the tibial plateau intercondylar eminence in the vertical direction, so that the physiological height of the knee joint femur after replacement is basically the same as the physiological height of the knee joint before replacement, and on this basis, the medial tibial plateau prosthesis 201 and the lateral tibial plateau prosthesis 202 are fixed, thus making the tibial prosthesis in a reasonable position to ensure a good patient experience after surgery.

When only the medial tibial plateau prosthesis 201 or the lateral tibial plateau prosthesis 202 of said tibial plateau prosthesis 2 is installed, said limiting hole extends into the tibial plateau intercondylar eminence 31, and does not penetrate said tibial plateau intercondylar eminence 31, that is, the intercondylar eminence hole 33 is a blind hole at this time.

Preferably, the width value of the tibial plateau intercondylar eminence 31 is less than or equal to the length value of the prosthetic notch 23.

In a preferred embodiment, as shown in FIG. 4, FIG. 5 and FIG. 6, the cross-sectional shape of the limiting hole 4 is consistent with the cross-sectional shape of the locating pin 5; the cross-sectional shape may be various shapes such as oval, square, trapezoid, rhombus, triangle, pentagon, pentagram, hexagon, octagon, etc. Among the various cross-sectional shapes of the locating pin, the use effect of triangle, square, trapezoid and polygons is better. In the present invention, a trapezoid is preferable, the trapezoidal upper bottom is located in the prosthetic notch 23, the lower bottom is located in the tibial notch 32, and the length of the upper bottom is greater than that of the lower bottom.

In a preferred embodiment, the cross-sectional size of said locating pin corresponds to the cross-sectional size of the limiting hole, and between both there is a close fit, preferably an interference fit; thereby making it difficult to continue to extend and got stuck after the locating pin is embedded to a certain depth. At this time, the locating pin just stays at desired position. Preferably, the position is the center position and will not deviate to both sides.

In a preferred embodiment, the cross-sectional size of said locating pin corresponds to the cross-sectional size of the limiting hole, and the locating pin can be embedded in a corresponding depth position of the limiting hole. Said locating pin may be provided with an expansion bolt on an end surface, and when the locating pin is located in desired position, preferably the center position, the expansion bolt is screwed so that the locating pin is locked and fixed in the limiting hole, thereby making sure that the locating pin is securely positioned and will not deviate to both sides.

In a preferred embodiment, the cross-sectional size of said locating pin is uniform, but the cross-sectional size of the limiting hole is changed. The locating pin is provided with an expansion bolt on an end surface and insert into the limit hole from the larger-sized side, after the locating pin is embedded to a certain depth and difficult to continue to extend, the locating pin can stay at the desired position, and at this time, the expansion bolt is screwed, so that the locating pin is stuck and fixed in the limiting hole making the locating pin fixed more stable.

In the present invention, said locating pin is one or more, and each locating pin is matched with a limiting hole. When there are multiple locating pins, there are also multiple limiting holes; the number of locating pins is consistent with that of limiting holes.

Said tibial plateau prosthesis 2 is placed at the position of the anterior upper end face of the tibia and the lower back of the patella. Preferably, the setting position of said tibial plateau prosthesis 2 is maintained at a predetermined distance from the lower edge of the patella, and the distance value between the natural tibial plateau and the patella is equal to the predetermined distance value. Replacing the natural tibial plateau with the tibial plateau prosthesis 2 has no substantial impact on the patella itself and does not affect the patella's sliding, which can ensure that the patella remains after surgery. The natural tibial plateau of the present application refers to a tibial plateau that grows naturally in a human body, where natural means naturally existence.

Figure 8:
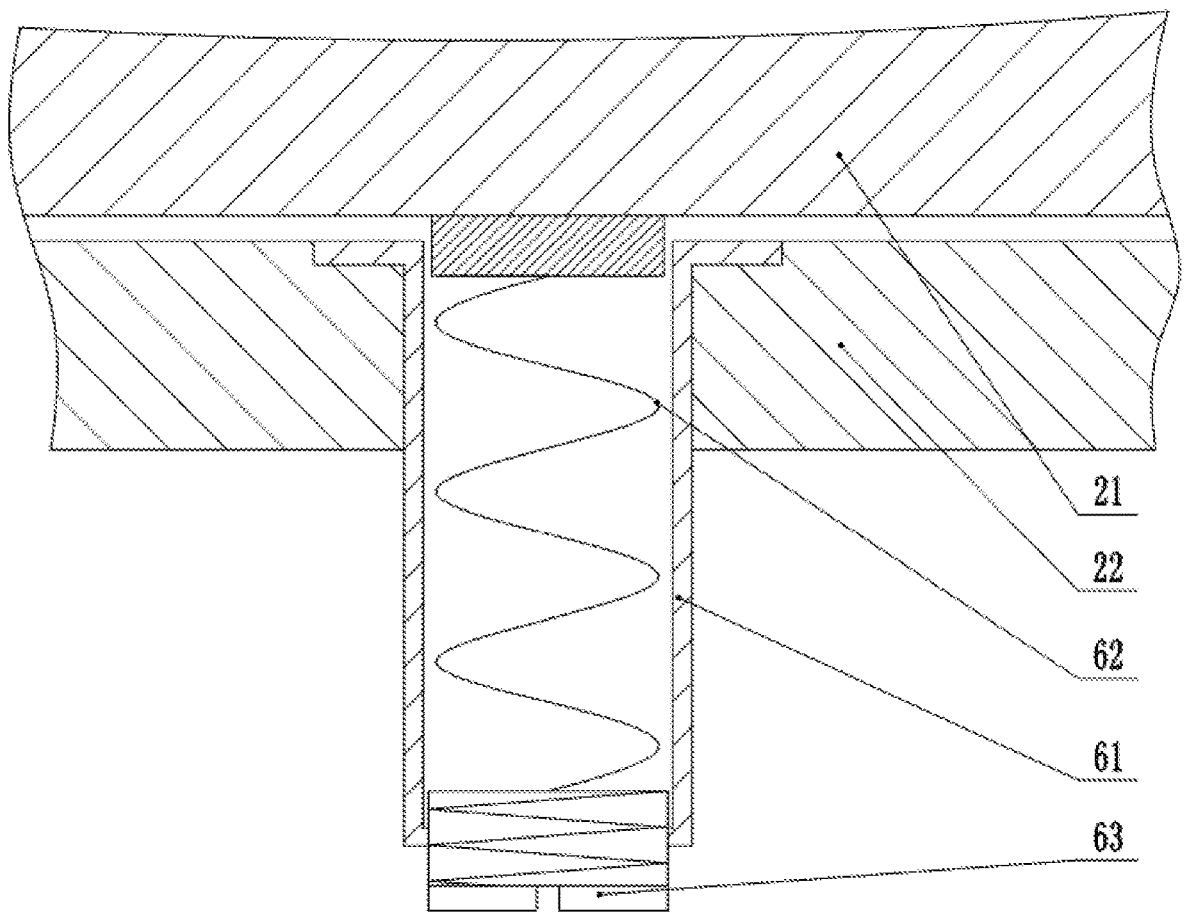
FIG. 8 shows a cross-sectional view of an elastic subassembly on a tibial plateau prosthesis in an artificial knee joint according to a preferred embodiment of the present invention.

In a preferred embodiment, said medial tibial plateau prosthesis 201 and lateral tibial plateau prosthesis 202 are substantially mirror-symmetric in a large configuration, but the size of each component is slightly different, and is completely copied according to the physiological structure of the human body, as shown in FIG. 7 and FIG. 8. Both said medial tibial plateau prosthesis 201 and said lateral tibial plateau prosthesis 202 include an upper gasket 21 and a lower gasket 22, and the upper gasket 21 and the lower gasket 22 are fixed by means of bolts, pin rolls and so on, thus making the upper gasket 21 and the lower gasket 22 have a certain relative displacement between them in the vertical direction and cannot be relatively moved in other directions.

An elastic subassembly 6 is provided on the lower gasket 22. The elastic subassembly 6 buffers the impact force transmitted from the femoral condyle prosthesis 1 to the upper gasket 21 of the tibial plateau prosthesis 2 so that the upper gasket 21 has a meniscus-like function. Said meniscus is cartilage tissue in a human knee joint that plays a role in buffering and shock absorption. Specifically, when the femoral condyle prosthesis 1 transmits an impact force to the tibial plateau prosthesis 2, the upper gasket 21 receives the impact force first, and cause the upper gasket 21 to move downward, thereby compressing the elastic subassembly 6, and as the reaction force of the elastic subassembly 6 gradually increases, the speed of the upper gasket 21 moves downward becomes smaller and smaller, and the impact force thereon also gets smaller and smaller, eventually the upper gasket presses against the lower gasket, and together transmits the force to the tibia. Due to the cushioning of the elastic subassembly 6, the force corresponding to the loss of the tibia can be ignored, thereby achieving a meniscus-like buffer effect, which is called to have a meniscus-like function.

In the present application, said elastic subassembly 6 may include a spring, and may also include a subassembly, such as an airbag, a cushion gasket and so on, that has certain elasticity and can play a role in cushioning and absorbing shock. The elastic subassembly 6 is disposed below the upper gasket 21 and can buffer the impact force transmitted from the upper gasket 21, and can select an appropriate specific placement position according to specific structural characteristics.

The following description uses an elastic subassembly including a spring as an example.

Said elastic subassembly 6 penetrates and is fixed on the lower gasket 22. A part of the elastic member 6 located above the lower gasket 22 is abutted on the lower surface of the upper gasket 21, and a part of the elastic subassembly 6 located below the lower gasket 22 is columnar.

Preferably, said elastic subassembly 6 specifically includes a sleeve 61 and a spring 62, as shown in FIG. 8.

Wherein, the lower end of the spring 62 is buried in the sleeve 61, and the upper end of the spring is abutted on the lower surface of the upper gasket, thus making the force transmitted from the femoral condyle prosthesis to the upper gasket 21 buffered by the spring 62 before acting on the lower gasket 22.

In the present invention, said prosthetic notch 23 is opened on the lower gasket 22.

In a preferred embodiment, said sleeve 61 is embedded in a cavity 7 opened on the tibia 3. Preferably, the cross-sectional shape of the cavity is consistent with the cross-sectional shape of the sleeve 61, and the cross-sectional size is also the same. The two can be closely fitted, so that the relative position between the tibia and the tibial plateau prosthesis is stable without relative displacement. The cross-sectional shapes of the sleeve 61 and the shape of the cavity 7 may be polygon, quadrangle, triangle, oval, circular, and so on. In the present invention, the cross-sectional shape is preferably circular.

Said sleeve can not only play a role in protecting the placement of the spring, but also can play a role in limiting and fixing the tibial plateau prosthesis 2, thereby making the overall structure of the tibial plateau prosthesis 2 simple and simplifying the process of placing and fixing the tibial plateau prosthesis.

In the present invention, preferably, said spring 62 is always in a non-stretched state.

In a preferred embodiment, as shown in FIG. 8, a bolt 63 is provided at the bottom of said sleeve 61, and the bolt 63 can move in the vertical direction as it rotates. Inside the sleeve 61, the top of said bolt is against the bottom of the spring 62, so that the elasticity of the spring 62 can be adjusted by controlling the position of the bolt 63 in the vertical direction. The bolt 63 moves upward in the vertical direction, the spring 62 is compressed, the elasticity of the spring 62 increases; the bolt 63 moves downward in the vertical direction, the degree of compression of the spring 62 decreases, and the elasticity of the spring 62 decreases, so that the appropriate spring elasticity or called spring tension can be adjusted according to the patient age and physical condition, the elasticity between the upper gasket 21 and the lower gasket 22 is consistent with the elasticity of the meniscus, the total height/thickness of the upper gasket 21 and the lower gasket 22 is consistent with the height of the side the artificial knee joint has not been replaced, and also the total height/thickness of the upper gasket 21 and the lower gasket 22 of the medial tibial plateau prosthesis 201 or the lateral tibial plateau prosthesis 202 is consistent with the height of the lateral tibial plateau prosthesis 202 or the medial tibial plateau prosthesis 201 replaced previously, thereby solving the problem of inconsistency in height and elasticity between the medial tibial plateau prosthesis 201 and the lateral tibial plateau prosthesis 202 that are replaced in two times, and making good effect after batch operation.

In a preferred embodiment, a scale line is engraved on the bottom of the sleeve 61 and/or near the bolt 63, so that the screwing degree of the bolt 63 can be read directly through the scale line, thereby facilitating the adjustment of the spring tension when placing the elastic subassembly 6.

Preferably, said spring 62 includes a top block provided on the top to contact the upper gasket 21.

In the present invention, said spring 62 may be made of materials such as metals and various high molecular polymers.

The present invention provides a method for using an artificial knee joint.

The artificial knee joint is the artificial knee joint described above, and the method includes the following steps:

Step 1, open a space for the placement of the tibial plateau prosthesis 2 on the tibial plateau. Preferably, when there is only one space, it is located on one side of the tibial plateau intercondylar eminence 31, and when there are two spaces, it is located at both sides of the tibial plateau intercondylar eminence 31. And in the process of opening the space, there is no damage to the tibial plateau intercondylar eminence 31 and the cruciate ligaments thereon, and further preferably, it will not cause damage to the patella and the quadriceps tendon where it is located.

Step 2, excavate a tibial notch 32 in the tibia and extend the tibial notch 32 to the tibial plateau intercondylar eminence 31; form an intercondylar eminence hole 33 on the tibial plateau intercondylar eminence 31; excavate a cavity 7 in the tibia. Preferably, the number of the tibial notch 32 and the cavity 7 is not fixed, and may be one, two or more, and preferably, both select one.

Step 3, insert the sleeve on the tibial plateau prosthesis 2 into the cavity 7, and simultaneously adjust the relative positions of the prosthetic notch 23, the tibial notch 32 and the intercondylar eminence hole 33 so that the prosthetic notch 23, the tibial notch 32 and the intercondylar eminence hole 33 together constitute a limiting hole 4.

Step 4, install the locating pin 5 into the limiting hole 4.

Step 5, fix the height position of the tibial plateau prosthesis 2 by the locating pin 5, and further fix the height of the tibial plateau prosthesis 2 by adjusting the injection amount of bone cement.

Preferably, before performing Step 3, adjust the elasticity of the spring 62 by rotating the bolt 63, wherein, the elasticity/strength of the spring is also detected by using an elasticity detection device to ensure that the elasticity/strength of the springs in the plurality of the elastic subassemblies 6 are consistent.

Preferably, it further includes the following optional steps:

Step a, assemble the upper gasket 21, the lower gasket 22, and the elastic subassembly 6 into a complete tibial plateau prosthesis 2, preferably, said tibial plateau prosthesis 2 includes a medial tibial plateau prosthesis 201 and/or a lateral tibial plateau prosthesis 202.

Step b, install the femoral condyle prosthesis 1, wherein, the femoral condyle prosthesis is fixed on the femur, located above the tibial plateau prosthesis and in contact with the tibial plateau prosthesis; preferably, excavate the prosthetic fixation area in said femur first, and then embed the femoral condyle prosthesis into this area. Because the femoral condyle prosthesis has a special curvature, an anterior button cover 11 and a posterior button cover 13, the femoral condyle prosthesis can be fastened to the femur, and at the same time, the fixing spine 12 on the femoral condyle prosthesis is inserted into the femur cancellous bone, the fixing pin 14 on the femoral condyle prosthesis is embedded in the blind hole excavated from the femur, so as to achieve the fixation between the femoral condyle prosthesis and the femur.

The present invention provides an artificial knee joint replacement method,

The artificial knee joint is the artificial knee joint described above, and the method includes the following steps:

Step 1, open a space for the placement of the tibial plateau prosthesis 2 on the tibial plateau. Preferably, when there is only one space, it is located on one side of the tibial plateau intercondylar eminence 31, and when there are two spaces, it is located at both sides of the tibial plateau intercondylar eminence 31. And in the process of opening the space, there is no damage to the tibial plateau intercondylar eminence 31 and the cruciate ligaments thereon, and further preferably, it will not cause damage to the patella and the quadriceps tendon where it is located.

Step 2, excavate a tibial notch 32 in the tibia and extend the tibial notch 32 to the tibial plateau intercondylar eminence 31; form an intercondylar eminence hole 33 on the tibial plateau intercondylar eminence 31; excavate a cavity 7 in the tibia. Preferably, the number of the tibial notch 32 and the cavity 7 is not fixed, and may be one, two or more, and preferably, both select one.

Step 3, insert the sleeve on the tibial plateau prosthesis 2 into the cavity 7, and simultaneously adjust the relative positions of the prosthetic notch 23, the tibial notch 32 and the intercondylar eminence hole 33 so that the prosthetic notch 23, the tibial notch 32 and the intercondylar eminence hole 33 together constitute a limiting hole 4.

Step 4, install the locating pin 5 into the limiting hole 4.

Step 5, fix the height position of the tibial plateau prosthesis 2 by the locating pin 5, and further fix the height of the tibial plateau prosthesis 2 by adjusting the injection amount of bone cement.

Preferably, before performing Step 3, adjust the elasticity of the spring 62 by rotating the bolt 63, wherein, the elasticity/strength of the spring is also detected by using an elasticity detection device to ensure that the elasticity/strength of the springs in the plurality of the elastic subassemblies 6 are consistent.

Preferably, it further includes the following optional steps:

Step a, assemble the upper gasket 21, the lower gasket 22, and the elastic subassembly 6 into a complete tibial plateau prosthesis 2, preferably, said tibial plateau prosthesis 2 includes a medial tibial plateau prosthesis 201 and/or a lateral tibial plateau prosthesis 202.

Step b, install the femoral condyle prosthesis 1, wherein, the femoral condyle prosthesis is fixed on the femur, located above the tibial plateau prosthesis and in contact with the tibial plateau prosthesis; preferably, excavate the prosthetic fixation area in said femur first, and then embed the femoral condyle prosthesis into this area. Because the femoral condyle prosthesis has a special curvature, an anterior button cover 11 and a posterior button cover 13, the femoral condyle prosthesis can be fastened to the femur, and at the same time, the fixing spine 12 on the femoral condyle prosthesis is inserted into the femur cancellous bone, the fixing pin 14 on the femoral condyle prosthesis is embedded in the blind hole excavated from the femur, so as to achieve the fixation between the femoral condyle prosthesis and the femur.

The present invention has been described above by combing the preferred embodiments; however, these embodiments are exemplary and only serve as illustrative. On the basis of the present invention, various replacements and improvements are permitted, and will be seen in the scope of the present invention.

What is claimed is:

1. An artificial knee joint according, characterized in that,
the knee joint includes a femoral condyle prosthesis (1) and tibial plateau prosthesises (2),
said tibial plateau prosthesises (2) include a medial tibial plateau prosthesis (201) and a lateral tibial plateau prosthesis (202) independently of each other,
the medial tibial plateau prosthesis (201) and the lateral tibial plateau prosthesis (202) are configured to be disposed at each side of a tibial plateau intercondylar eminence, respectively, and the medial tibial plateau prosthesis (201) and the lateral tibial plateau prosthesis (202) are located below the femoral condyle prosthesis (1);
the artificial knee joint further includes a locating pin (5), through said locating pin (5) the medial tibial plateau prosthesis (201) and the lateral tibial plateau prosthesis (202) are fixed to the upper end of the tibia;
the medial tibial plateau prosthesis (201) and the lateral tibial plateau prosthesis (202) are configured to include an upper gasket (21) and a lower gasket (22), respectively, wherein, an elastic subassembly (6) is provided on the lower gasket (22), and through which the impact force transmitted from the femoral condyle prosthesis (1) to an upper gasket of the tibial plateau prosthesis (2) is cushioned, so that the upper gasket (21) has a meniscus-like function;

said elastic subassembly (6) penetrates the lower gasket (22), and is fixed and installed on the lower gasket (22), an upper end of elastic subassembly (6) protrudes above the lower gasket (22) and abuts on lower surface of the upper gasket.

2. The artificial knee joint according to claim 1, characterized in that, said locating pin (5) is configured to pass through the tibial plateau intercondylar eminence, an upper portion of one end of locating the pin (5) is installed in the medial tibial plateau prosthesis (201), and an upper portion of other end of locating the pin (5) is installed in the lateral tibial plateau prosthesis (202).

3. The artificial knee joint according to claim 1, characterized in that, a prosthetic notch (23) is provided between bottoms of said medial tibial plateau prosthesis (201) and said lateral tibial plateau prosthesis (202), a tibial notch is configured to be provided on top of the tibia below the tibial plateau prosthesis (2), and said prosthetic notch (23) and the tibial notch (32) are configured to together constitute a limiting hole (4) for accommodating the locating pin (5), and the limiting hole is configured to penetrate the tibial plateau intercondylar eminence.

4. The artificial knee joint according to claim 1, characterized in that, said elastic subassembly (6) includes a sleeve (61) and a spring (62), a lower end of the spring (62) is buried in the sleeve (61), and an upper end of the spring is abutted on lower surface of the upper gasket, the sleeve (61) passes through the lower gasket (22), and a bottom end of the sleeve is configured to be installed in a cavity of the tibia.

5. The artificial knee joint according to claim 4, characterized in that, a bolt (63) for adjusting the elasticity of the spring (62) is provided at bottom of the sleeve (61).

* * * * *